United States Patent
Moody et al.

(10) Patent No.: US 9,750,905 B2
(45) Date of Patent: Sep. 5, 2017

(54) BREATHING ASSISTANCE APPARATUS

(75) Inventors: Paul Moody, Auckland (NZ); Bronwyn Nicola Cotter, Auckland (NZ); Neil Prime, Auckland (NZ); Glenn Whyte, Auckland (NZ); Matthew Jon Payton, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 676 days.

(21) Appl. No.: 10/357,753

(22) Filed: Feb. 4, 2003

(65) Prior Publication Data

US 2004/0040559 A1    Mar. 4, 2004

(30) Foreign Application Priority Data

Feb. 4, 2002  (NZ) ........................................ 517030
Apr. 10, 2002  (NZ) ........................................ 518289

(51) Int. Cl.
*A62B 9/02*    (2006.01)
*A61M 16/00*   (2006.01)
(Continued)

(52) U.S. Cl.
CPC ........ *A61M 16/00* (2013.01); *A61M 16/0463* (2013.01); *A61M 16/208* (2013.01);
(Continued)

(58) Field of Classification Search
CPC .... A61M 16/00; A61M 16/20; A61M 16/208; A61M 16/209; A61M 2240/00;
(Continued)

(56) References Cited

U.S. PATENT DOCUMENTS 1,162,416 A    11/1915 Teter
1,632,449 A    6/1927  McKesson
(Continued)

FOREIGN PATENT DOCUMENTS

DE    31 42 830    3/1983
DE    195 32 042   5/1996
(Continued)

OTHER PUBLICATIONS

"PressCut Industries" Technical Bulletin, http:web.archive.org/web/20010125074600/http://presscut.com/pctb9603.htm, Jan. 25, 2001.

*Primary Examiner* — Victoria J Hicks
(74) *Attorney, Agent, or Firm* — Knobbe, Martens, Olson & Bear, LLP (57) ABSTRACT

A pressure regulating device includes a housing having an inlet, a main outlet, an J an external venting outlet. An internal venting aperture is between the inlet and the external venting outlet. A valve is between the external venting outlet and the internal venting aperture. When the pressure of gases in the flow path is below a predetermined level, the valve at least partially blocks the internal venting aperture. When the pressure is above the predetermined level, the valve opens to allow at least a portion of the gases to flow from the inlet through the internal venting aperture and the external venting outlet. The valve is shaped to open in such a manner that the portion of gases flowing varies with the flow rate, such that the pressure at the main outlet is substantially constant over the flow rate range.

11 Claims, 9 Drawing Sheets

(51) Int. Cl.
*A61M 16/04* (2006.01)
*A61M 16/20* (2006.01)
*A61M 16/08* (2006.01)

(52) U.S. Cl.
CPC . *A61M 16/0816* (2013.01); *A61M 2202/0488* (2013.01); *A61M 2240/00* (2013.01)

(58) Field of Classification Search
CPC .......... A61M 16/0463; A61M 16/0816; A61M 16/0833; A61M 16/0084; A62B 9/02; A62B 9/022; F16K 15/148
USPC ............ 128/205.24, 204.18, 204.25, 204.26, 128/204.27, 205.13–205.19, 207.14, 128/207.15, 207.16, 202.28, 202.29, 128/203.11, 201.28, 207.12; 137/907, 137/908
See application file for complete search history.

(56) References Cited

U.S. PATENT DOCUMENTS

| | | | |
|---|---|---|---|
| 2,099,841 A * | 11/1937 | Connell | A61M 16/104 128/205.12 |
| 2,834,339 A | 5/1958 | Bennett et al. | |
| 3,152,604 A * | 10/1964 | Frye | F16K 24/042 137/202 |
| 3,799,185 A * | 3/1974 | Milnes et al. | 137/102 |
| 3,807,445 A | 4/1974 | McPhee | |
| 4,655,213 A | 4/1987 | Rapoport et al. | |
| 5,207,220 A | 5/1993 | Long | |
| 5,301,667 A | 4/1994 | McGrail | |
| 5,437,272 A * | 8/1995 | Fuhrman | 128/203.12 |
| 5,735,271 A * | 4/1998 | Lorenzen | A61M 16/0463 128/200.26 |
| 5,746,199 A | 5/1998 | Bayron et al. | |
| 5,762,063 A | 6/1998 | Coates et al. | |
| 5,839,436 A * | 11/1998 | Fangrow et al. | 128/205.24 |
| 6,006,748 A | 12/1999 | Hollis | |
| 6,041,775 A | 3/2000 | Century | |
| 6,058,933 A * | 5/2000 | Good et al. | 128/205.13 |
| 6,067,984 A | 5/2000 | Piper | |
| 6,086,529 A | 7/2000 | Arndt | |
| 6,202,645 B1 | 3/2001 | Brown | |
| 6,453,940 B1 * | 9/2002 | Tipton | F04B 53/1092 137/493.9 |
| 6,629,530 B2 | 10/2003 | Cise | |
| 6,634,378 B2 * | 10/2003 | Semeia | 137/505.25 |
| 6,886,561 B2 | 5/2005 | Bayron et al. | |
| 6,959,709 B2 * | 11/2005 | Curran et al. | 128/205.29 |
| 6,997,206 B1 * | 2/2006 | Klockseth et al. | 137/102 |
| 7,207,332 B1 | 4/2007 | Lugtigheid | |
| 7,341,059 B2 | 3/2008 | Moody et al. | |
| 2003/0000529 A1 * | 1/2003 | Kay | 128/204.26 |
| 2003/0062040 A1 * | 4/2003 | Lurie et al. | 128/203.11 |
| 2004/0040559 A1 | 3/2004 | Moody et al. | |
| 2004/0089302 A1 * | 5/2004 | Foss | 128/204.18 |
| 2004/0094157 A1 * | 5/2004 | Dantanarayana et al. | 128/206.21 |
| 2004/0149286 A1 * | 8/2004 | Haston | 128/204.26 |
| 2005/0000517 A1 * | 1/2005 | Eriksson et al. | 128/203.12 |
| 2006/0090759 A1 * | 5/2006 | Howes et al. | 128/204.21 |
| 2006/0185674 A1 * | 8/2006 | Hollis | 128/205.24 |

FOREIGN PATENT DOCUMENTS

| | | |
|---|---|---|
| EP | 0 911 050 | 4/1999 |
| FR | 1580403 | 9/1969 |
| FR | 2709066 | 2/1995 |
| GB | 2222778 | 3/1990 |
| WO | WO 00/22985 | 4/2000 |

* cited by examiner

BREATHING ASSISTANCE APPARATUS

FIELD OF INVENTION

The present invention relates to the use of a pressure regulator in conjunction with a breathing assistance apparatus, particularly though not solely, for regulating the pressure of gases supplied to a patient from a Positive End Expiratory Pressure (PEEP) apparatus or for an infant resuscitation device.

BACKGROUND

At the moment of their first breath, a baby's lungs are collapsed and filled with fluid. The pressures needed to open such lungs, and keep them open, are several times that of a normal breath until the fluid is displaced and the lungs have filled with air. To generate these large pressures, the baby must have strong respiratory muscles, as well as a chemical called surfactant in their alveoli. Surfactant reduces the surface tension of the fluid within the alveoli, preventing the alveolar walls from sticking to each other, like coasters to coffee cups when there is water between them.

Neonates have difficulty in opening their lungs and keeping them open. Reasons for this include:

a) Weak respiratory muscles and low surfactant levels. This means that they cannot generate enough pressure to open the lungs and, should they be resuscitated, tire quickly with the effort of keeping open alveoli lacking in surfactant.

b) Underdeveloped internal tissue structure to support the alveoli.

c) Slower clearance of lung fluid. In very premature neonates, fluid may continue to be secreted in the alveoli even after birth.

d) A soft chest wall, horizontal ribs, and a flatter diaphragm contribute to reduce the inspiratory capacity.

e) The mixing of oxygenated and deoxygenated blood raises blood pressure in the lungs, increasing fluid movement from the blood vessels into the lung tissue. The reduced blood oxygen level starves tissue of oxygen and further weakens respiratory muscles.

f) Weak neck muscles and a lack of neck fat reduce upper airway stability so that collapse on inspiration may occur.

g) Collapsed, damaged alveoli secrete proteins that reduce surfactant function.

To alleviate this it is known to apply Positive End Expiratory Pressure (PEEP) during respiration, resuscitation or assisted respiration (ventilation). In applying PEEP, the neonate's upper airway and lungs are held open during expiration against a pressure that stops alveolar collapse. Lung fluid is pushed back into the circulating blood, alveolar surfactant is conserved, and a larger area of the lung participates in gas exchange with the blood. As blood oxygenation and carbon dioxide removal improves, more oxygen is delivered to growing tissues, while less oxygen and energy is consumed by respiratory muscles. In the case of resuscitation or ventilation the pressure is varied between a Peak Inspiratory Pressure (PIP) and the PEEP value until the patient/infant is breathing spontaneously.

In order to provide the PEEP across a range of flow rates, some method is required to regulate the pressure. It is known in the art to provide a valve near the infant, which actuates at a level of pressure (ie: the PEEP value) to allow the gases to vent externally.

Such valves may employ a spring-loaded valve, which in turn requires the use of high quality springs, which have been individually tested to give a high tolerance spring constant in order to ensure that it actuates at a value substantially that of the maximum safe pressure. Both the manufacture and testing of such a spring necessitates that its cost will be correspondingly high. Accordingly it would be advantageous to provide a pressure relief valve for a breathing assistance system which did not involve the use of such a high tolerance spring.

Figure 4A:
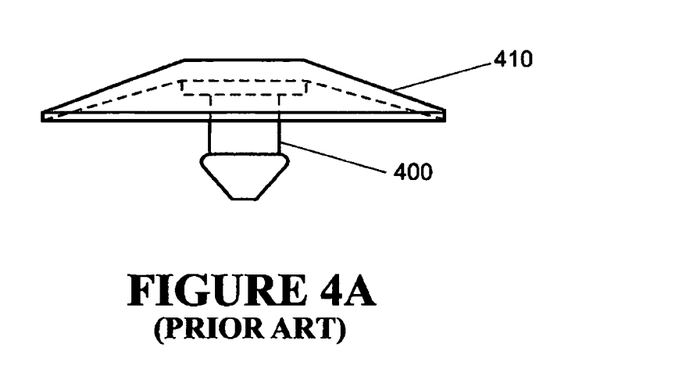
FIG. 4a is aside view showing hidden detail of a prior art umbrella valve.
Figure 4B:
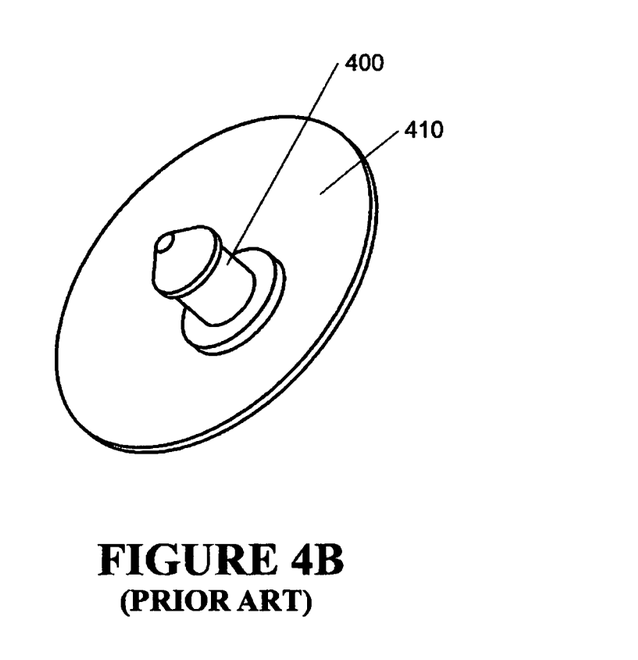
Figure 5:
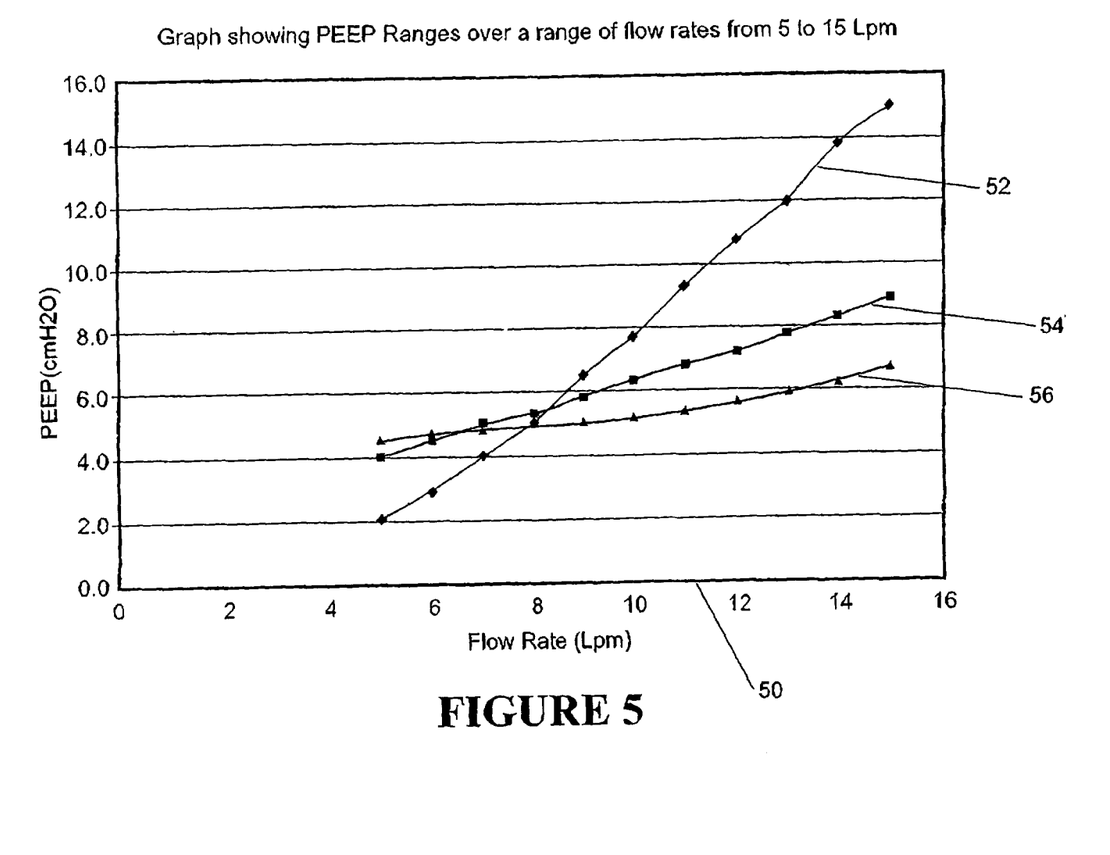
FIG. 5 is a graph showing a comparison of the pressure ranges produced by different types of valves over a flow range of 5-15 liters/minute.

Also such valves are known to have substantial variation of the relief pressure with flow rate. For example as seen in FIG. 5 the delivered pressure is shown for a range of valves. Over a given range of flow rates shown in the graph 50 of FIG. 5, a variable orifice valve as shown by line 52 gives a wide range of delivered pressure. An improvement on this is a prior art umbrella valve (for example the "umbrella check valve" manufactured by Vernay Laboratories Inc. shown in FIGS. 4a & 4b) which delivers a lower variation in delivered pressure, as shown by line 54. However in all cases the variation in delivered pressure of prior art valves would desirably be reduced for this application.

SUMMARY OF INVENTION

It is an object of the present invention to provide a pressure regulator which goes some way to achieving the above-mentioned desiderata or which will at least provide the Healthcare industry with a useful choice.

Accordingly, in a first aspect, the present invention consists in a pressure regulating device for use with a breathing assistance and/or resuscitation apparatus, said apparatus supplying gases over a flow rate range to an infant or neonate requiring resuscitation and/or breathing assistance, said pressure regulating device comprising:

a housing including an inlet, a main outlet, and an external venting outlet, the housing defining a flow path between said inlet and said main outlet, said inlet adapted to be in fluid communication or integrated with said breathing assistance and/or resuscitation apparatus and said main outlet adapted to be in fluid communication with an infant, and an internal venting aperture between said inlet and said external venting outlet, a valve member disposed within said housing, between said external venting outlet and said internal venting aperture, wherein when the pressure of gases in the flow path is below a predetermined level, said valve member at least partially blocks said internal venting aperture, said gases thereby flowing from said inlet to said main outlet, and wherein when said pressure of said gases is above said predetermined level, said valve member opens to allow at least a portion of said gases to flow from said inlet through said internal venting aperture and said venting outlet, said valve member having a shape such that it will open to allow a portion of said gases flowing from said inlet through said internal venting aperture, said portion varying with said flow rate, such that the pressure at said main outlet is kept at a reasonably constant level over said range of flow provided by said resuscitation apparatus.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

The invention consists in the foregoing and also envisages constructions of which the following gives examples.

BRIEF DESCRIPTION OF THE DRAWINGS

One preferred form of the present invention will now be described with reference to the accompanying drawings in which:

FIG. 4b is a perspective view of the prior art umbrella valve of FIG. 4a.

DETAILED DESCRIPTION OF THE PREFERRED EMBODIMENTS

The present invention is a connector including a valve, for use when resuscitating an infant or neonate. The delivered pressure is varied between Peak Inspiratory Pressure (PIP) and Peak End Expiratory Pressure (PEEP) by the occlusion of a PEEP outlet on the valve. The PEEP outlet may either allow variable PEEP, by adjustment, or substantially flow independent fixed PEEP using a novel umbrella valve. In the preferred embodiment, a duck billed valve is included for suctioning of surfactant delivery during resuscitation. In the preferred embodiment, the connector is adapted for one handed use. If using the fixed PEEP valve, this avoids the need for adjustment as flow through the valve changes, and provides more effective therapy.

Figure 1:
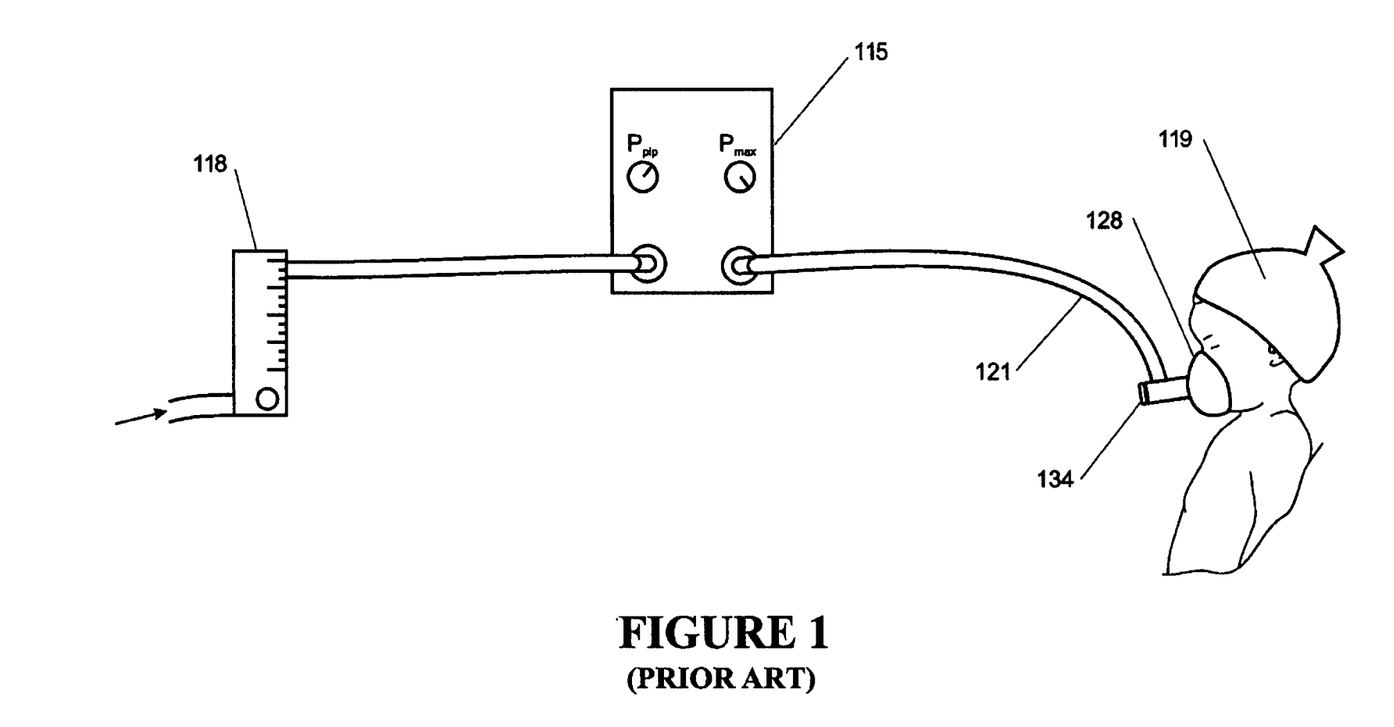
FIG. 1 is a block diagram showing a typical configuration for supplying breathing assistance to a neonate in accordance with the prior art.

Referring now to FIG. 1 a typical application as known in the prior art is depicted. A Positive End Expiratory Pressure (PEEP) system is shown in which an infant 119 is receiving pressurized gases through a nasal mask 128 (or endotracheal tube or other interface as are known in the art) connected to an inhalatory conduit 121, preferably for resuscitation. Either the mask 128 or the inhalatory conduit 121 can include the pressure regulator 134 of the present invention, to control the pressure of gas delivered to the infant. The inhalatory conduit 121 is connected to the outlet of a resuscitator apparatus 115, which is in turn connected to a flow regulator and air supply 118 (which provides gas to the resuscitator at 50 psi or thereabouts).

It should be understood that the present invention, however, is not limited to resuscitation, or the delivery of PEEP gases but is also applicable to other types of gas delivery systems.

Pressure Regulator

Figure 2A:
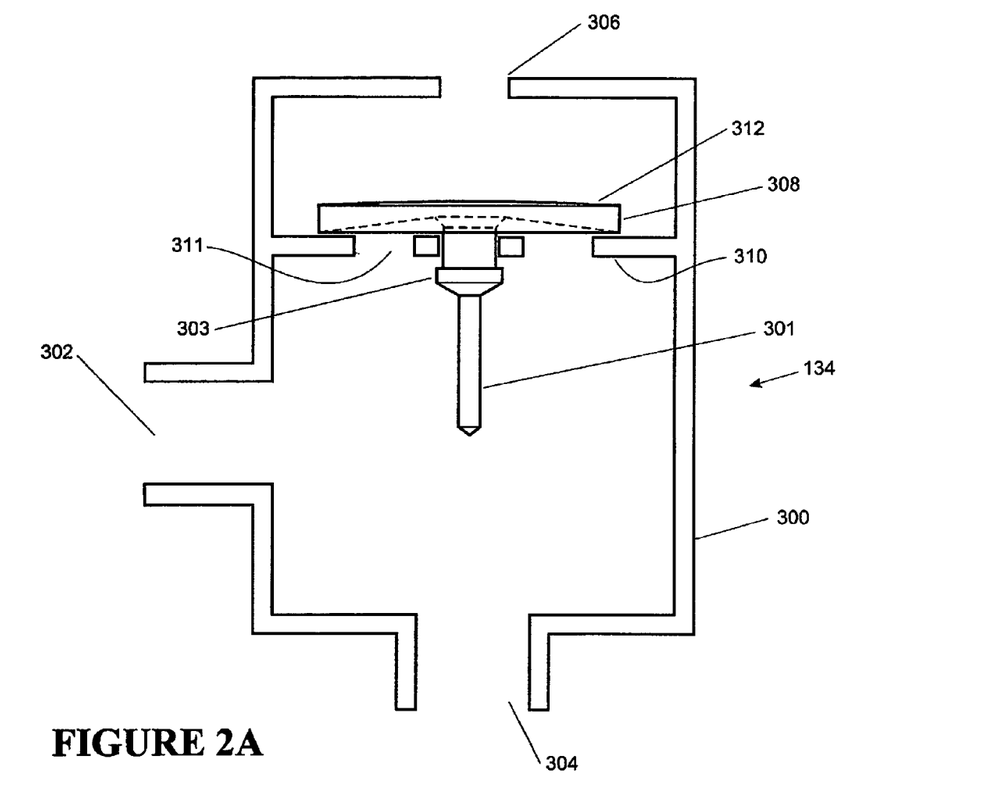
FIG. 2a is a sectional view of a typical layout of a pressure regulator that can be used with the apparatus of FIG. 1, according to the preferred embodiment of the present invention.
Figure 2B:
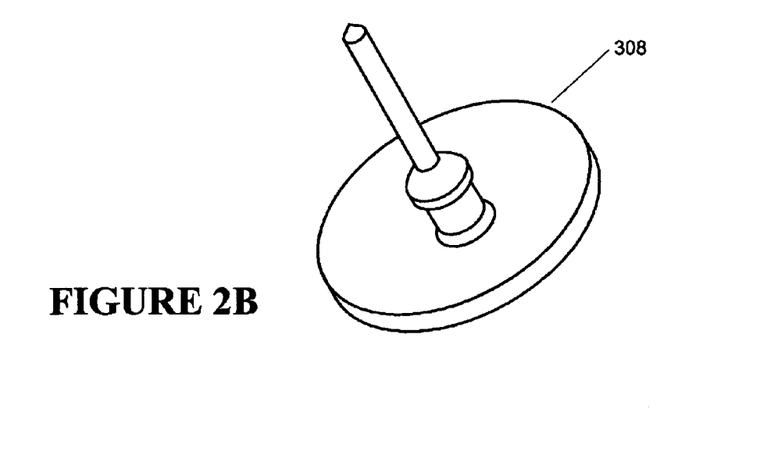
FIG. 2b is a perspective view of a valve member used with the pressure regulator of FIG. 2a, according to the preferred embodiment of the present invention.
Figure 3:
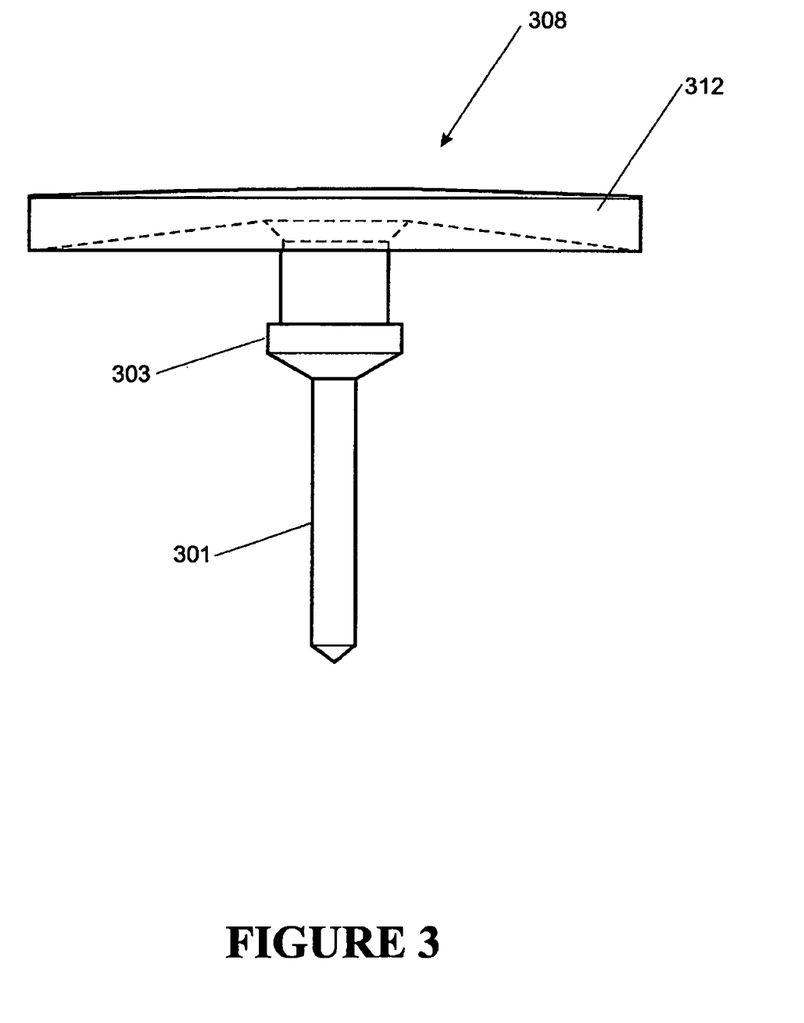
FIG. 3 is a side view showing hidden detail of the valve member of FIG. 2b, according to the preferred embodiment of the present invention.

The preferred embodiment of the pressure regulator 134 of the present invention is shown in FIGS. 2 and 3 in detail. In the preferred embodiment the regulator 134 is disposed within a mask 128 although it will be appreciated that it can be located in a separate assembly, so long as it is proximate the infant.

Referring particularly to FIG. 2a we see a cross-sectional schematic of the preferred embodiment of the pressure regulator 134. The pressure regulator 134 includes a housing or manifold 300 with an inlet 302 and two outlets 304, 306. The first outlet 304 supplies respiratory gases to the infant. The second outlet 306 is an external orifice which, as described previously, can be used to vary pressure between PIP and PEEP. Located between the inlet 302 and the orifice 306 is an improved PEEP valve 308.

The PIP is adjusted at the resuscitator 115 to a desired level. The gases delivered to the infant 119 are varied between the PIP (with orifice 306 near the infant occluded), and the PEEP (with the orifice 306 un-occluded, so that a portion of the gas from the resuscitator 115 flows through the orifice 306). It can be seen that resuscitation of an infant can be attempted by varying the pressure at outlet 304 between the PIP and PEEP at a normal respiratory frequency.

The purpose of the PEEP valve 308 is to keep the Positive End Expiratory Pressure (PEEP) at a reasonably constant level, independent of changes in the overall flow rate of gases from resuscitator 115.

It is desirable for infant respiratory assistance that the PEEP value should be approximately 5 cmH$_2$0, independent of the flow rate. Preferably interfaces of the type used for resuscitation need to be simple and cost effective, as these are single-use products. Also, due to the nature of this application, a valve with many small separate parts, such as a spring valve, is not a viable option.

In the preferred embodiment, the PEEP valve 308 is a small umbrella valve 308, made of an elastomeric material, and positioned on a valve seat 310 as shown particularly in FIGS. 2a & 2b. Valve seat 310 defines an internal venting aperture 311 which is covered and closed by the valve 308 in a closed position. Preferably the valve 308 and seat 310 are included as part of the nasal mask 128, or as part of an endotracheal tube (not shown). As the overall flow rate is increased, the consequent increase in pressure inside the manifold 300 causes the umbrella valve flaps 312 to lift up from the valve seat 310, thereby letting more air out from inside the manifold 300, and therefore keeping the pressure inside the manifold 300 at a constant level.

The umbrella valve 308 of the present invention differs from other prior art umbrella valves in the material and dimensions, the material being Silastic liquid silicone rubber Q7-4840. The overall proportions of the umbrella valve are as shown in FIG. 3. In particular, comparing FIG. 3 to the prior art valve shown in FIGS. 4A and 4B, we see the present invention has a characteristic flap 312 which is thicker at the periphery than at the centre. The ratio of the centre thickness to the periphery thickness should be 2:3, giving the cross-sectional shape shown in FIG. 3. The valve 308 of the present invention includes a shaft 301, which has a retaining flange 303.

Due to the design used, the umbrella valve 308 of the present invention does not act as a 'pop-off' valve. Most umbrella valves such as that shown in FIGS. 4A and 4B are designed to open at a specific 'cracking pressure'. The prior art valve shown in FIGS. 4A and 4B has a shaft 400 and flap 410. Often prior art valves have a "cracking pressure which will increase as the flow threshold increases". In contrast, the valve of the present invention is designed to open at a predetermined flow rate (in this specific application above 5 liters/minute) and will continue to open further as the flow rate increases, increasing the flow through the internal aperture 311, and thus causing the pressure in the manifold 300 to remain constant as the flow from resuscitator 115 increases. Most prior art umbrella valves will open at a certain pressure level and do not open any further with an increase in flow rate. This causes the pressure in a manifold to increase as the flow from a resuscitator increases.

The improved characteristics of the present invention can be seen in FIG. 5. If using a simple variable orifice valve, if the flow rate is changed between 5 and 15 liters per minute a dramatic change in PEEP will also occur, as shown by line 52. The PEEP range for the variable orifice valve is 13 cmH$_2$O. In tests, the best result obtained from prior art umbrella valves, as shown by line 54, was a PEEP range of 4.9 cmH$_2$O In the same tests, the best result gained from the valve of the present invention as shown by line 56 is a PEEP range of 2.8 cmH$_2$O.

Figure 6:
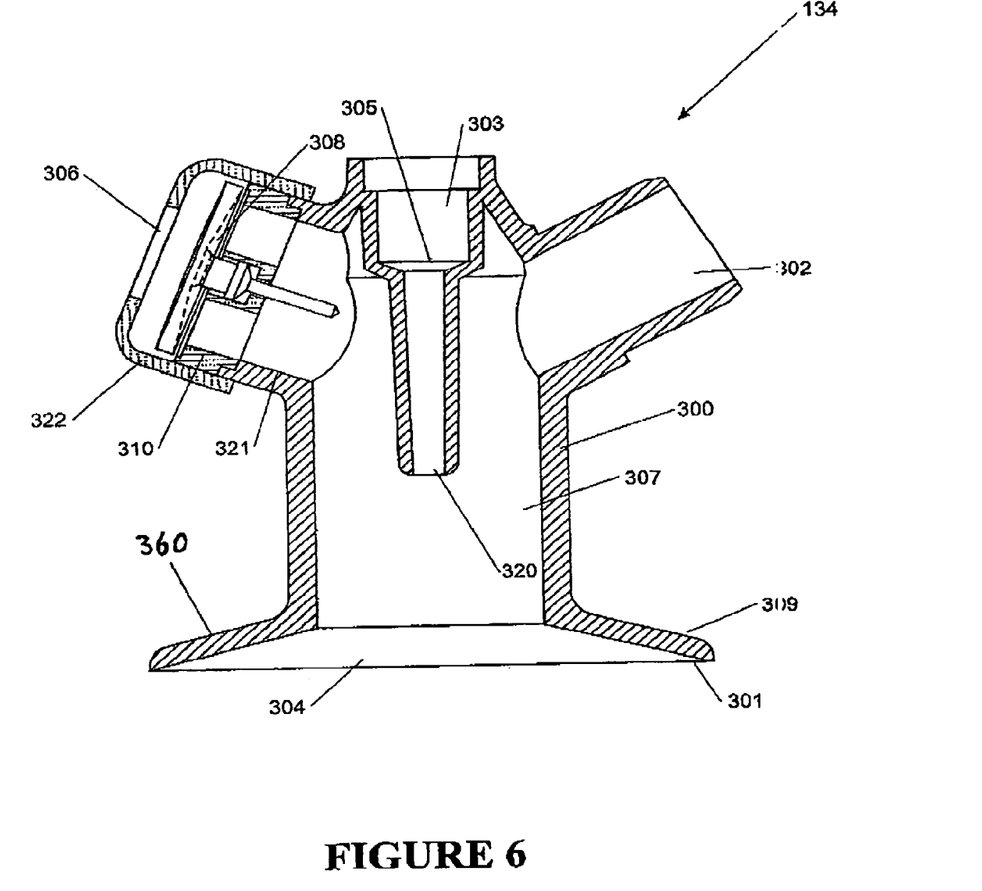
FIG. 6 is a sectional front elevation view of a pressure regulator according to a further embodiment of the present invention.
Figure 7:
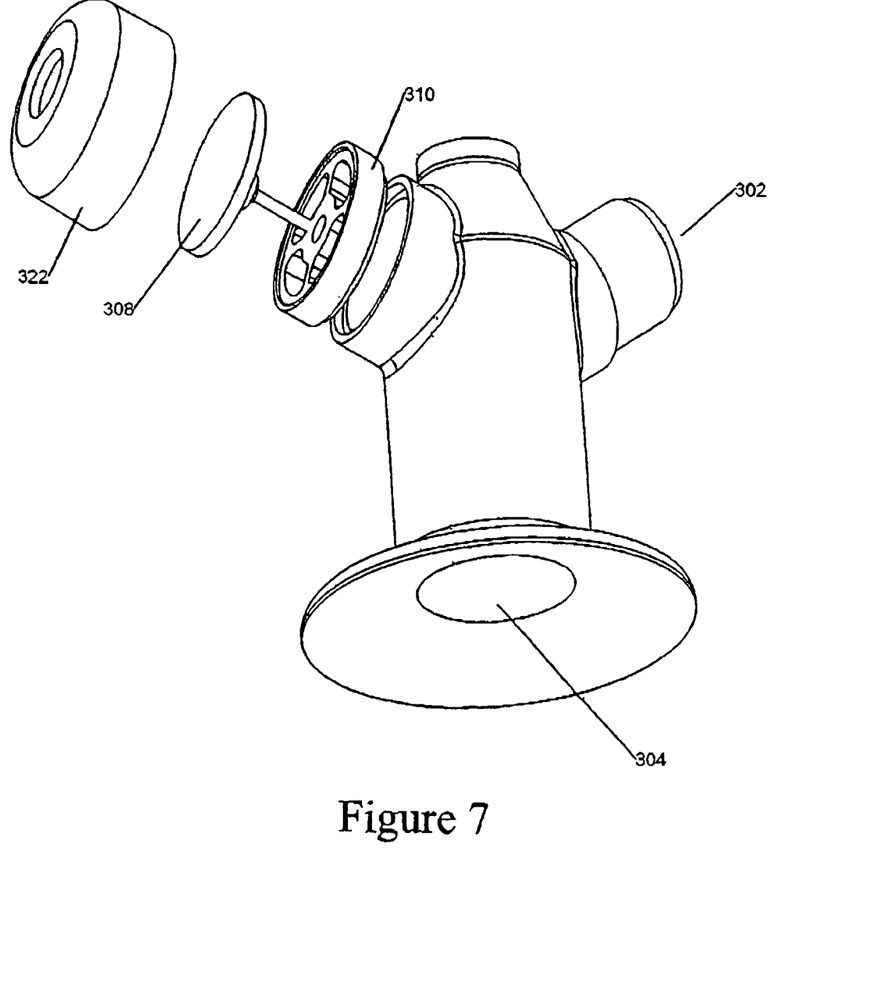
FIG. 7 is an exploded perspective view of the pressure regulator of FIG. 6.

Referring to FIG. 6 we see an alternate embodiment of the pressure regulator 134. Located between the inlet 302 and the orifice 306 is a PEEP valve 308, preferably the umbrella valve described previously for the preferred embodiment. Included in this alternate embodiment is an inlet 303 which includes a duck billed valve 305, used for introducing tubes down the trachea of the infant 119, for suctioning, delivery of surfactant etc. The duck-billed valve 305 is normally closed.

In this alternate embodiment, the manifold 300 is shaped to enable ease of use; and it is designed to enable one handed operation. The manifold 300 is preferably wide and short and in this embodiment, shown in FIG. 6, it has a generally cylindrical cross-section. At the outlet 304 to the neonate, which is connected to the manifold 300, is a flange 301. When the present invention is used with a mask, the flange 301 enables the operator to apply pressure, pushing the mask into position to seal the mask around the neonate's nose and mouth. The flange 301 also enables an operator to use one digit on their hand to occlude orifice 306, in order that they can vary pressure in the manifold 300 between PIP and PEEP. The operator achieves this variation in the pressure most easily by placing their thumb and middle finger on the flange 301 at 309 and 360 and then using their index finger to seal orifice 306. The orifice branch 321 is shown at an angle 309 to the manifold 300. This angle 309 allows the index finger to be placed in a natural position to occlude orifice 306. The previously described embodiment of the pressure regulator 134 operates in the same way as the embodiment described above.

As has already been described, new born neonates often lack surfactant in their lungs. When the present invention is used with an endotracheal tube, surfactant can be administered to a patient without the need to remove the breathing assistance apparatus from the patient. By using a syringe or similar, the operator can administer surfactant to the neonate by pushing the end of the syringe through the duck billed valve 305, located opposite the inlet 301, and administer the surfactant to the infant 119.

The duck billed valve 305 is normally sealed against the passage of fluids, but upon insertion of a syringe, the duck-billed valve 305 opens to allow the syringe end to enter the interior of the manifold 307. The bill, or inner end 320, of the duck billed valve 305 seals around the end of an inserted syringe, ensuring that the manifold 300 remains sealed. The valve bills 320 is manufactured from a silicone rubber, or other suitable material as known in the art. It is known that surfactant is a viscous fluid, and therefore this method of administration is advantageous over the method of administering surfactant using multi lumen endotracheal tubes.

The duck billed valve 305 can also be used to suction a neonate or infant 119, to remove airway secretions. Suctioning is performed using a catheter inserted through the duck billed valve 305, inserting the catheter through the duckbilled valve 305, then down the endotracheal tube. The bill 320 of the valve 305 seals around an inserted catheter so that airway pressure is maintained. The duckbilled valve 305 is retained in the manifold 300 in such a way that any instrument inserted into the valve 305 is guided directly into the top of an endotracheal tube (or alternatively, a nasal mask, or other interfaces as are known in the art), one end of the endotracheal tube fitted at the outlet 304.

Figure 8:
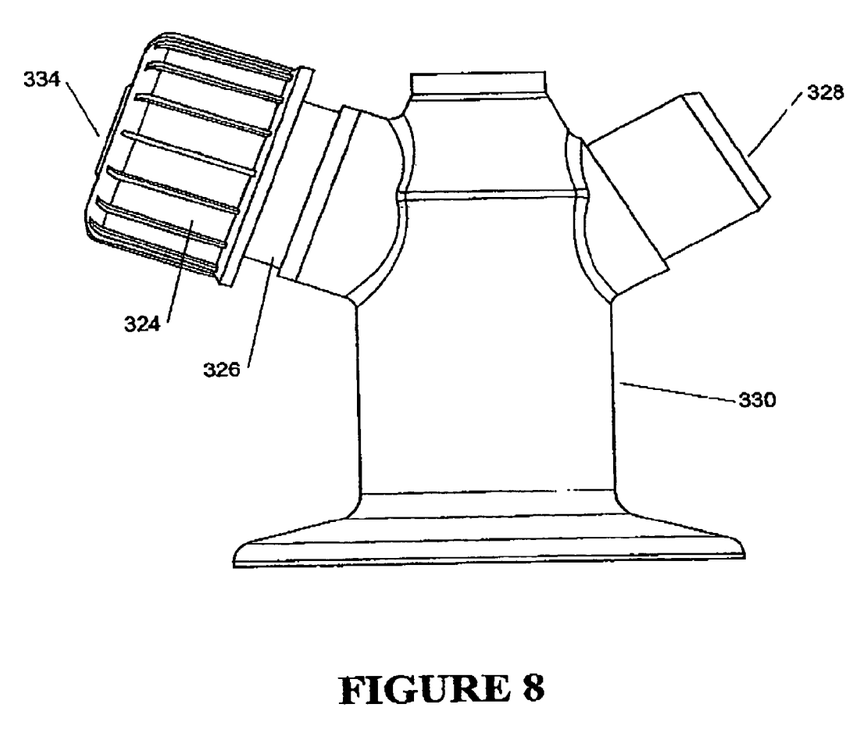
FIG. 8 is a front elevation of a pressure regulator according to a still further embodiment of the present invention.
Figure 9:
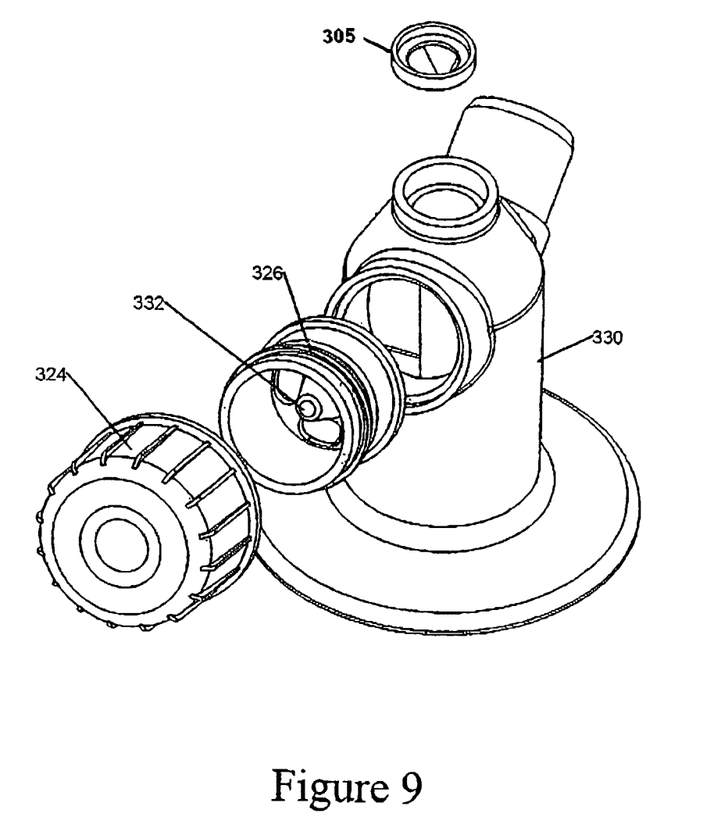
FIG. 9 is an exploded perspective view of the pressure regulator of FIG. 8.

FIG. 8 and FIG. 9 illustrate a further alternate embodiment of the pressure regulator 134. The overall shape of the manifold 330 is similar to that previously described with reference to FIG. 6, with, in this embodiment, orifice branch 321 is replaced by an alternate orifice branch 326. The pressure of the delivered gases is varied between PIP, with orifice 334 on branch 326 occluded, and PEEP, with the orifice 334 un-occluded. As is best shown with reference to FIG. 9, the manifold 330 includes a jet outlet 332 positioned between the inlet 328 and the outlet orifice 334. The flow rate of the gases through the jet outlet 332 is controlled by a screw-on cap 324, which is located screwed onto a thread on the end of the outlet branch 326 of the manifold 330. The traveled distance of the screw on cap on the thread determines the restriction to the orifice 332 and therefore varies the PEEP. That is, the closer the screw on cap 324 is to the jet outlet 332, the smaller the gas flow rate through the orifice 334. The manifold 330 is otherwise as described for the previous embodiments.

The invention claimed is:

1. A pressure regulating device for use with a breathing assistance and/or resuscitation apparatus, said apparatus being capable of supplying gases to an infant or neonate requiring breathing assistance and/or resuscitation, said pressure regulating device comprising:
   a housing comprising:
      an inlet adapted to be in fluid communication or integrated with said breathing assistance and/or resuscitation apparatus;
      a main outlet adapted to in use be in fluid communication with the infant or neonate;
      an external venting outlet configured to be occluded and un-occluded to vary a pressure at said main outlet between a peak inspiratory pressure (PIP) with said external venting outlet occluded and a peak end expiratory pressure (PEEP) with said external venting outlet un-occluded such that a portion of said gases flows through said external venting outlet to vent externally; and
      an internal venting aperture extending through a wall and having a perimeter;
   said housing defining a first flow path between said inlet and said main outlet and a second flow path between said inlet and said external venting outlet, said internal venting aperture positioned in said second flow path between said inlet and said external venting outlet such that gases in said second flow path flow from said inlet through said wall within the perimeter of the internal venting aperture to said external venting outlet, and an umbrella valve disposed within said housing in said second flow path between said external venting outlet and said internal venting aperture, a flap of said umbrella valve having a periphery positioned against said internal venting aperture, so that when a pressure of gases in said first flow path is below a predetermined level, said umbrella valve at least partially blocks said internal venting aperture, said gases thereby flowing from said inlet to said main outlet, and wherein when said pressure of said gases is above said predetermined level, said umbrella valve opens to allow a portion of said gases to flow from said inlet through said internal venting aperture and said external venting outlet, said flap having a cross-sectional shape such that a central portion of said flap is thinner in cross-sectional width than said periphery.

2. A device as claimed in claim 1, wherein a ratio of said cross-sectional width of said central portion to said cross-sectional width of said periphery is 2:3.

3. A device as claimed in claim 2, wherein said umbrella valve has a shaft adapted to engage said housing, said shaft attached to or integral with a substantially central portion of said flap.

4. A device as claimed in claim 3, wherein said shaft includes an annular flange adapted to retain said umbrella valve within said housing.

5. A device as claimed in claim 1, wherein said umbrella valve has a shaft adapted to engage said housing, said shaft attached to or integral with said central portion of said flap.

6. A device as claimed in claim 5, wherein said shaft includes an annular flange adapted to retain said umbrella valve within said housing.

7. A device as claimed in claim 1 wherein said flap of said umbrella valve extends continuously across said internal venting aperture when said pressure of gases in said flow path is below said predetermined level.

8. A device as claimed in claim 1 wherein said pressure regulating device is attached to a mask.

9. A device as claimed in claim 1, wherein said cross-sectional shape of said flap is formed so that as said umbrella valve opens, said portion of said gases varies with flow rate in such a manner that the PEEP at said main outlet remains within a range of 2.8 $cmH_2O$ over a flow rate range between 5 and 15 liters per minute provided by said breathing assistance and/or resuscitation apparatus.

10. A device as claimed in any one of claim 1, 2, 6, or 3 wherein said housing also includes an aperture adapted to receive a surfactant delivery tube or suctioning tube, said aperture including a sealing valve which in use allows said surfactant delivery tube or suctioning tube to access the infant or neonate while also preventing an interior of said housing from fluidically communicating with external atmosphere via said aperture.

11. A device as claimed in claim 10, wherein said sealing valve is a duck billed valve.

* * * * *